US006268345B1

(12) United States Patent
Grinna

(10) Patent No.: US 6,268,345 B1
(45) Date of Patent: *Jul. 31, 2001

(54) BACTERICIDAL/PERMEABILITY-INCREASING PROTEIN (BPI) COMPOSITIONS

(75) Inventor: Lynn S. Grinna, Upperville, VA (US)

(73) Assignee: Xoma Corporation, Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/502,286

(22) Filed: Feb. 11, 2000

Related U.S. Application Data

(63) Continuation of application No. 09/299,321, filed on Apr. 26, 1999, now Pat. No. 6,057,293, which is a continuation of application No. 08/251,576, filed on May 31, 1994, now Pat. No. 5,932,544.

(51) Int. Cl.[7] .................................................. A61K 38/16
(52) U.S. Cl. .............................. 514/12; 514/21; 530/350
(58) Field of Search ........................ 514/12, 21; 530/350

(56) References Cited

U.S. PATENT DOCUMENTS

| | | | |
|---|---|---|---|
| 3,839,314 | 10/1974 | Fekete et al. | 260/112 B |
| 4,478,829 | 10/1984 | Landaburu et al. | 424/177 |
| 4,719,239 | 1/1988 | Muller et al. | 514/785 |
| 4,933,179 | 6/1990 | Allison et al. | 424/89 |
| 4,997,664 | 3/1991 | Williams | 426/392 |
| 5,030,448 | 7/1991 | Hunter | 424/83 |
| 5,037,664 | 8/1991 | Shaked et al. | 424/85.2 |
| 5,039,520 | 8/1991 | Hunter | 424/83 |
| 5,041,288 | 8/1991 | Hunter | 424/83 |
| 5,071,649 | 12/1991 | Hunter | 424/78.38 |
| 5,089,274 | 2/1992 | Marra et al. | 424/534 |
| 5,096,885 | 3/1992 | Pearlman et al. | 514/12 |
| 5,118,528 | 6/1992 | Fessi et al. | 427/213.36 |
| 5,118,794 | 6/1992 | Grangeorge et al. | 530/363 |
| 5,133,908 | 7/1992 | Stainmesse et al. | 264/4.1 |
| 5,152,979 | 10/1992 | Hunter | 424/78.38 |
| 5,171,739 | 12/1992 | Scott | 514/12 |
| 5,182,106 | 1/1993 | Mezrow et al. | 424/78.31 |
| 5,198,541 | 3/1993 | Elsbach et al. | 435/69.1 |
| 5,234,683 | 8/1993 | Hunter et al. | 424/78.31 |
| 5,234,908 | 8/1993 | Szabo et al. | 514/12 |
| 5,234,912 | 8/1993 | Marra et al. | 514/21 |
| 5,308,834 | 5/1994 | Scott et al. | 514/12 |
| 5,334,584 | 8/1994 | Scott et al. | 514/12 |
| 5,348,942 | 9/1994 | Little, II et al. | 514/12 |
| 5,439,807 | 8/1995 | Grinna | 435/69.1 |
| 5,932,544 | * 8/1999 | Grinna | 514/12 |
| 6,057,293 | * 5/2000 | Grinna | 514/12 |

FOREIGN PATENT DOCUMENTS

| | | |
|---|---|---|
| WO 88/06038 | 8/1988 | (WO) . |
| WO 89/01486 | 2/1989 | (WO) . |
| WO 92/03535 | 3/1992 | (WO) . |
| WO 92/09621 | 6/1992 | (WO) . |
| WO 92/16484 | 10/1992 | (WO) . |
| WO 92/19250 | 11/1992 | (WO) . |
| WO 93/06228 | 4/1993 | (WO) . |
| WO 93/23434 | 11/1993 | (WO) . |
| WO 93/23540 | 11/1993 | (WO) . |
| WO 94/17819 | 8/1994 | (WO) . |

OTHER PUBLICATIONS

FDA, Division of Drug Information Resources, "Inactive Ingredient Guide" including list of "Currently Marketed Injectable Products," (1991).

FDA review and basis for approval of OB–NDA–86–0909 on FLUOSOL® (20% Intravascular Perflorochemical Emulsion), The Green Cross Corp. (1989).

Gazzano–Santoro, et al., "High–Affinity Binding of the Bactericidal/Permeability–Increasing Protein and a Recombinant Amino–Terminal Fragment to the Lipid A Region of Lipopolysaccharide," *Infection and Immunity*, vol. 60, 4754–4761, (Nov., 1992).

Genentech, Inc., "A Tissue Plasminogen Activator," Product Information (1987).

Gray, et al., "Cloning of the cDNA of a Human Neutrophil Bactericidal Protein," *The Journal of Biological Chemistry*, vol. 264, No. 16, 9505–9509 (Jun. 5, 1989).

The Green Cross Corporation, "Peruflorochemical Blood Substitutes," Technical Info. Series Nos. 5 & 7 (1978 and 1981).

Henson, et al., "The Surface Coagulation of Proteins During Shaking," *J. Colloid & Interface Sci.*, 32(1):162–165 (Jan. 1970).

ICI Americas, Inc., "ICI Americas Products For Cosmetics and Pharmaceuticals," Chapters 1–4, pp. 1–39 (1977).

ICI Americas, Inc., "The HLB System," Chapters 1–8, pp. 3–20 (1984).

Kaplan and Fraser, "Formation of Fibres from Protein Monolayers," *Nature*, 171(4352):559–560 (Mar. 28, 1953).

Krantz, et al., "Sugar Alcohols," *Bulletin of School of Medicine, U. of MD*, 36:48–56 (1951).

Levine, et al., "The Use of Surface Tension Measurements in the Design of Antibody–Based Product Formulations," *J. Parenteral Sci. & Tech.*, 45(3):160–165 (May–Jun. 1991).

MacRitchie, "Proteins at Interfaces," *Adv. Protein Chem.*, 32:283–326 (1978).

Neugebauer, "A Guide to the Properties and Uses of Detergents in Biology and Biochemistry," Calbiochem® Brand Chemicals, Hoechst Celanese Corp. (1987).

(List continued on next page.)

Primary Examiner—Chhaya D. Sayala
(74) Attorney, Agent, or Firm—Marshall, O'Toole, Gerstein, Murray & Borun

(57) ABSTRACT

Bactericidal/permeability increasing protein (BPI) and biologically active fragments, analogs and variants thereof are solubilized by lipid carriers including phospholipids, liposomes and nonionic detergents and stabilized against particle formation by poloxamer surfactants.

2 Claims, 10 Drawing Sheets

OTHER PUBLICATIONS

Ooi, et al., "Endotoxin–neutralizing Properties of the 25 kD N–Terminal Fragment and a Newly Isolated 30 kD C–Terminal Fragment of the 55–60 kD Bactericidal/Permeability–increasing Protein of Human Neutrophils," *J. Exp. Med.,* vol. 174, 649–655 (Sep., 1991).

ORTHO Pharmaceutical Corporation, "Orthocolone OKT–3," Product Information Package Insert (1986).

The U.S. Pharmacopeia USPXXII, pp. 1763, 1857, and NFXVII, pp. 1960–1961, 1967–1968.

Wang, et al., "Parenteral Formulations of Proteins and Peptides: Stability and Stabilizers," *J. Parenteral Sci. Tech.,* 42(Supp. 25):S4–526 (1988).

Weiss, et al., "Cellular and Subcellular Localization of the Bactericidal/Permeability–Increasing Protein of Neutrophils," *Blood,* vol. 69, No. 2, 652–659 (Feb., 1987).

Weiss, et al., "Resistance to Gram–negative Bacteria to Purified Bactericidal Leukocyte Proteins", *J. Clin. Invest.,* 65:619–628 (Mar., 1980).

Wyandotte Chemicals Corporation, "Information on Applications of Pluronics," pp. 1–13 (Mar. 1, 1952).

* cited by examiner

BACTERICIDAL/PERMEABILITY-INCREASING PROTEIN (BPI) COMPOSITIONS

This is a Continuation of U.S. application Ser. No. 09/299,321, filed Apr. 26, 1999 now U.S. Pat. No. 6,057,293 which is a continuation of U.S. application Ser. No. 08/251,576 filed May 31, 1994, now U.S. Pat. No. 5,932,544.

BACKGROUND OF THE INVENTION

The present invention relates to the solubilization and stabilization of bactericidal/permeability-increasing protein (BPI) and biologically active polypeptide fragments, analogs and variants thereof. More particularly, the invention provides compositions of BPI and such BPI-related polypeptides with lipids and, particularly, lipid carrier substances such as phospholipids, liposomes and nonionic detergents as well as compositions with poloxamer surfactants. Also provided are improved pharmaceutical compositions for use as parenteral drugs.

Recent advances in the development of genetic engineering technology have made a wide variety of biologically active polypeptides available in sufficiently large quantities for use as drugs. Recombinant BPI and fragments, analogs and variants of BPI, like other polypeptides, can be subject to particulate formation and loss of biological activity by a variety of chemical and physical means including denaturation due to heating or freezing and exposure to extreme pH or other chemical degradation. Particulate formation and loss of biological activity can occur as a result of physical agitation and interactions of polypeptide molecules in solution and at the liquid-air interfaces during the process of isolation and upon storage within vials. It is believed that the polypeptide molecules adsorb to an air-liquid interface, unfolding to present hydrophobic groups to air with the hydrophilic groups immersed in the aqueous phase. Once so positioned at the surface, the polypeptide molecules are susceptible to aggregation, particle formation and precipitation. It is also believed that further conformational changes can occur in polypeptides adsorbed to air-liquid and solid-liquid interfaces during compression-extension of the interfaces such as occurs from agitation during compression-extension of the interfaces such as occurs from agitation during transportation or otherwise. Such agitation can cause the protein to entangle, aggregate, form particles and ultimately precipitate with other adsorbed proteins. Particle formation due to surface denaturation can be somewhat controlled by appropriate selection of the dimensions of storage vials and by minimizing the air volume (headspace) in those vials. In this regard, partially filled containers represent the worst case for vibration induced precipitation.

Particle formation has traditionally been controlled by incorporation of surfactants into the protein-containing composition in order to lower the surface tension at the solution-air interface. Classic stabilization of pharmaceuticals by surfactants or emulsifiers (e.g., lipid carriers) has focused on the amphipathic nature of molecular groups containing both hydrophilic and hydrophobic properties within the surfactant molecule.

Wang et al., J. Parenteral Sci. & Technol., 42, supp. 25, pp. S4–S26 (1988) review the use of surfactants as stabilizers for proteins and peptides in parenteral drug formulations. Specifically, polysorbate 20 and polysorbate 80 are cited as stabilizers for pharmaceutical compositions including those containing interleukin-2, tissue plasminogen activator and tumor necrosis factor. Wang et al. further disclose the use of BRIJ surfactants for the stabilization of pharmaceutical compositions comprising uricase and insulin and the use of an otherwise uncharacterized poloxamer surfactant for the stabilization of an insulin composition. Of interest to the present invention is the work related to use of polysorbate 80 (TWEEN 80), poloxamer-188 (PLURONIC F-68) and steareth-100 (BRIJ 700) for stabilization of antibody-based product formulations as described in Levine, et al., J. Parenteral Sci. Technol., 45, 3, 160–165 (1991). A monoclonal antibody product, OKT3 (Ortho Pharmaceutical Corp.) approved by U.S. regulatory authorities for human use is formulated with polysorbate 80.

Although a variety of surfactants or emulsifiers have been used to solubilize/stabilize polypeptide compositions, regulatory requirements limit the types and specific identities of surfactants that can be incorporated into parenteral compositions for injection into the human body. Generally accepted surfactants having a history of use and listed in the U.S. Pharmacopoeia XXII include polysorbate (polyoxyethylene sorbitol ester) and poloxamer (polyoxypropylene-polyoxyethylene block copolymer) polymers. Polysorbate 80 has been approved in parenteral solutions for over 20 years, but is rarely used in concentrations greater than 0.1% in solution volumes of 100 mL or more. For example, Krantz et al., "Sugar Alcohols - XXVIII. Toxicologic, Pharmacodynamic and Clinical Observations on TWEEN 80," Bull. of the School of Med., U. of Md., 36, 48 (1951), identifies the onset of hemolysis in the dog for a polysorbate concentration of 0.1% at 90 minutes. In addition, neonatal deaths have been associated with the use of polysorbate 80 at concentrations of greater than 1%. With respect to poloxamer surfactants, the highest safe concentration for poloxamer 188 in approved parenteral solutions was 2.7% in an approved parenteral use blood substitute perfluorochemical solution where it was diluted as much as 10 fold in the bloodstream. Thus, certain concentrations of surfactants may pose increased risk of toxic effects, earlier onset of hemolysis, and observed changes in both neutrophils and platelets, which are involved in blood complement activation.

BPI and fragments, analogs and variants of BPI are susceptible to particulate formation and loss of biological activity. Nevertheless, the art has failed to show means for the stabilization of such BPI polypeptides or for the solubilization of BPI polypeptide aggregates, particles or precipitates. Accordingly, there exists a need in the art for BPI compositions providing improved protein solubilization and stability. Moreover, there exists a need in the art for pharmaceutical compositions comprising BPI or biologically active fragments, analogs or variants thereof which comprise only concentrations of components which are regarded as safe and are included in parenterals approved by regulatory authorities for commercial use.

SUMMARY OF THE INVENTION

The present invention provides compositions comprising a bactericidal/permeability-increasing protein (BPI) or a biologically active polypeptide fragment, analog or variant thereof (produced by recombinant or nonrecombinant means) and a lipid carrier, particularly a nonionic detergent lipid carrier, where the BPI polypeptide is solubilized in the lipid carrier. Useful nonionic detergent lipid carriers include octoxynol-9 (TRITON X-100, Rohm & Haas), polysorbate 80 (TWEEN 80, ICI Americas, Inc., Wilmington Del.), polysorbate 20 (TWEEN 20, ICI Americas, Inc.) and laureth-4 (BRIJ 30, ICI Americas, Inc.). The nonionic detergent lipid carriers, such as polysorbate 80 solubilize/ stabilize BPI polypeptides by altering (generally lowering) the surface tension of the polypeptide solution. The invention also provides a method of solubilizing/stabilizing such BPI polypeptides by contacting the polypeptide with a lipid carrier under conditions such that the polypeptide is solubilized.

The invention additionally relates to the discovery that a poloxamer surfactant is particularly useful for the solubilization/stabilization of compositions comprising an aqueous solution of BPI protein or biologically active fragments, analogs, or variants of BPI protein. The invention provides a method of solubilizing/stabilizing such polypeptides without altering the surface tension by contacting the polypeptide solution with a poloxamer surfactant, for example, poloxamer 188. The poloxamer surfactant component is preferably present in a concentration of from about 0.01% to about 1% by weight with a concentration of 0.1% to 0.2% by weight being preferred to stabilize protein solutions comprising less than or equal to 2 mg/mL.

The invention further relates to compositions comprising a bactericidal/permeability-increasing protein (BPI) or a biologically active polypeptide fragment, analog or variant thereof and a phospholipid or liposome lipid carrier wherein the polypeptide is solubilized.

DETAILED DESCRIPTION

Figure 1:
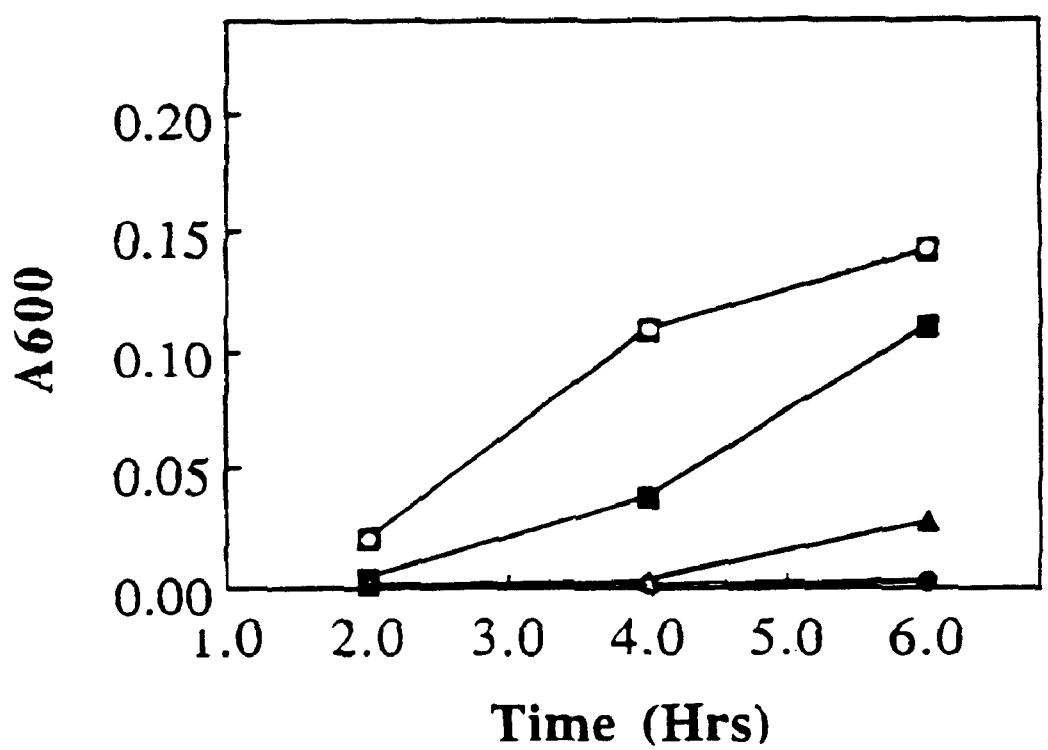
FIGS. 1 and 2 graphically represent the results of bacterial growth inhibition assays for $rBPI_{23}$ with and without polysorbate 20 surfactant addition.

The present invention provides methods and materials for maintaining the solubility/stability of BPI polypeptide compositions with lipid carriers, particularly nonionic detergent lipid carriers, phospholipid and liposome lipid carriers, and with poloxamer surfactants. The invention further provides methods and materials for maintaining the solubility/stability of BPI polypeptide pharmaceutical compositions using only concentrations of components which are regarded as safe and are included in parenterals approved by regulatory authorities for commercial use. Specifically, the invention relates to the discovery that nonionic detergent molecules provide improvements in solubilization and stabilization of BPI and biologically active fragments, analogs and variants thereof. The invention also relates to the discovery that poloxamer surfactants have unique properties in the solubilization/stabilization of such BPI-related proteins. It is believed that poloxamer surfactants protect BPI and fragments, analogs and variants thereof from surface denaturation by stabilizing unfolded and partially unfolded BPI polypeptide molecules and preventing precipitation of those molecules, and not by altering the surface tension of the BPI solution.

BPI and biologically active fragments, analogs and variants thereof useful with the present invention include recombinantly produced proteins such as described e.g., in U.S. Pat. No. 5,198,541. Co-owned, copending patent application Theofan et al., U.S. patent application Ser. No. 08/064,693 filed May 19, 1993, which is a continuation-in-part application of U.S. Ser. No. 07885,911 filed May 19, 1992, addresses BPI-Immunoglobulin fusion proteins which are variants of BPI protein comprising at the amino terminal a BPI protein or a biologically active fragment thereof, and retaining the same biological activity of BPI protein. The disclosures of these patent applications are incorporated by reference herein. Particularly preferred BPI analog materials include recombinant polypeptides produced according to co-owned and copending Theofan et al. U.S. patent application Ser. No. 08/013,801 filed Feb. 2, 1993 and entitled "Stable Bactericidal/Permeability-Increasing Protein Products and Pharmaceutical Compositions Containing the Same," the disclosure of which is herein incorporated by reference. A preferred BPI fragment is characterized by about 1 to 199 or about 1 to 193 of the amino-terminal amino acid residues of the mature human BPI molecule as set out in Gray et al., J. Biol. Chem., 264, 9505–9509 (1989) except that residue 185 is glutamic acid rather than lysine as specified in Gray. The recombinant expression product of DNA encoding BPI amino acids 1 to 199 has been designated $rBPI_{23}$. The recombinant expression product of DNA encoding BPI amino acids 1 to 193 has been designated rBPI(1–193). A preferred BPI fragment analog comprises the first 193 amino acid residues as set out in Gray except that residue 185 is glutamic acid rather than lysine and the cysteine at position 132 is replaced with a non-cysteine residue such as alanine. Such a protein is designated $rBPI_{21}$ or $rBPI(1–193)ala^{132}$.

The present invention provides a composition comprising BPI and biologically active fragments, analogs and variants thereof and a lipid carrier. A pharmaceutically acceptable lipid carrier is preferred for use in medicinal products designed for internal use.

As used in this application a lipid carrier is any fat soluble substance which inhibits protein precipitation. Lipid carriers may comprise sterile solutions and gels. Compositions comprising such lipid carriers are formulated by well known conventional methods.

The lipid carrier may be a phospholipid, a liposome, a lipopolysaccharide (such as bacterial endotoxin), a fatty acid or a detergent. As used herein, a detergent is any substance that alters the surface tension of a liquid, generally lowering it. The detergent may be a nonionic detergent. Examples of nonionic detergents include octoxynol-9 (TRITON X-100, Rohm & Haas), polysorbate 80 (TWEEN 80, ICI Americas, Inc., Wilmington Del.), polysorbate 20 (TWEEN 20, ICI Americas, Inc.) and laureth-4 (BRIJ 30, ICI Americas, Inc.). Preferred nonionic detergents are polysorbate 80 and polysorbate 20.

A preferred polysorbate nonionic detergent preferably has a surface tension between 10 and 70 mN/m as measured in aqueous solution at room temperature and at a concentration of 0.1%. More preferably, the polysorbate is characterized by a hydrophilic/lipophilic balance (HLB) value of about 15 and by a surface tension between 40 and 50 mN/m as measured in aqueous solution at room temperature and at a concentration of 0.1%. Most preferred is polysorbate 80 (sorbitan mono-9-octadeconoate) which is available commercially as TWEEN 80 (ICI Americas, Inc.).

Poloxamer surfactants are members of the group of polyoxypropylene-polyoxyethylene block copolymers and are characterized by having generally hydrophilic properties. Poloxamer surfactants are believed to promote solubilization/stabilization of BPI and fragments, analogs and variants thereof by a mechanism that does not involve altering the surface tension of the BPI polypeptide solution. Poloxymer surfactants are believed to protect the polypeptide from surface denaturation by stabilizing unfolded and partially unfolded BPI polypeptide molecules.

Preferred poloxamer surfactants are characterized by a HLB value greater than about 14 and a surface tension between 10 and 70 mN/m as measured in aqueous solution at room temperature and at a concentration of 0.1%. More preferred is a poloxamer surfactant which has a HLB value between about 25 and 35 and has a surface tension between 30 and 52 mN/m as measured in aqueous solution at room temperature and at a concentration of 0.1%. Most preferred is poloxamer 188 available commercially as PLURONIC F-68 (BASF Wyandotte, Parsippany, N.J.), which is characterized by a surface tension of 50 mN/m and by an HLB value of 29.

The invention will be better understood upon consideration of the following illustrative examples of practice thereof wherein: Example 1 addresses solubilization of solutions of recombinant products with a variety of materials including phospholipids, liposomes and nonionic detergents; Example 2 addresses biological activities of recombinant products in compositions with polysorbate 20; Examples 3 and 4 address tests of various surfactants to determine their utility for surface stabilization of $BPI_{23}$; Example 5 addresses evaluation of the surface activity of polysorbate and poloxamer surfactants alone or in solutions of $rBPI_{21}$; and Example 6 addresses Differential Scanning Calorimetry (DSC) analysis of $rBPI_{21}$ solutions prepared with polysorbate and poloxamer surfactants.

EXAMPLE 1

In this example, the effects of various methodologies for stabilizing solutions of recombinant BPI proteins produced by transfected CHO cells were examined. It was found that when $rBPI_{23}$ was eluted from S-Sepharose beads with a sodium chloride/acetate buffer, the resulting BPI preparation contained significant amounts of hairy, thread-like or filamentous precipitates. Addition of nonionic detergents to the buffer used to elute $rBPI_{23}$ solubilized the protein and prevented formation of the hairy, thread-like precipitates, but increased the quantities of other contaminants eluted. Addition of nonionic detergents to eluted $rBPI_{23}$ preparations containing the hairy, thread-like precipitates decreased the size and number of the precipitates. Phospholipids were mixed with an $rBPI_{23}$ solution and a solution of full-length recombinant BPI was sonicated with liposome kit materials. Elution of $rBPI_{23}$ directly into a solution comprising a nonionic detergent prevented formation of the thread-like precipitates and avoided elution of other contaminants from the cell culture medium.

1(A). Eluting $rBPI_{23}$ with Buffer Containing Nonionic Detergents

In this experiment, different methods were used to elute $rBPI_{23}$ from S-Sepharose beads that had been cultured in roller bottles with CHO cells transfected with DNA encoding the 31-residue signal sequence and amino acids 1 to 199 of mature BPI protein. The procedures were carried out according to the general method of Example 1 of co-owned and co-pending U.S. patent application Ser. No. 08/072,063 filed May 19, 1993 which is a continuation-in-part of U.S. patent application Ser. No. 07/885,501, the disclosures of which are hereby incorporated by reference. See also, PCT WO 93/23540 published Nov. 25, 1993. Specifically, S-Sepharose beads from five roller bottles of transfected CHO cells were separated from cells and culture media with a millipore filter and washed with 20 mM sodium acetate/acetic acid, 100 mM NaCl pH 4.0 (Buffer). The washed beads were resuspended into 15 mL fractions and each fraction was treated with a different eluting solution. The eluting solutions were (1) Buffer with 0.7 M and 1.0 M NaCl; (2) 0.1% polysorbate 20 in Buffer with 0.7 M, 1.0 M and 1.5 M NaCl; (3) 0.1% polysorbate 80 in Buffer with 0.7 M, 1.0 M and 1.5 M NaCl; (4) 0.5% octoxynol-9 (TRITON X-100) in Buffer with 1.0 M NaCl; and (5) a taurine isopropanol solution with 0.35 M, 0.7 M and 1.0 M NaCl.

The eluate obtained using Buffer and sodium chloride alone (No. 1, above) contained significant amounts of hairy, thread-like precipitates. Polysorbate 20, polysorbate 80, octoxynol-9 (TRITON X-100), and taurine protected BPI from formation of thread-like precipitates on elution. These eluates, however, also contained increased quantities of culture medium contaminants.

1(B). Treatment of $rBPI_{23}$ Samples with Nonionic Detergents and Lipid Carriers After Elution Samples of $rBPI_{23}$ protein solutions containing thread-like precipitates were contacted with a variety of agents to assess the ability of the agent to dissipate or dissolve the precipitate. In one experiment, two mL aliquots of the solutions were placed in 15 mL screw cap tubes. The various agents, including phospholipid, TWEEN 80, TWEEN 20 and TRITON X-100, were added, mixed by hand, and visually compared to control (untreated) samples. The results are set out in Table 1, which reflects the approximate concentration of the agent added. Agents which appeared to prompt formation of additional thread-like precipitates are indicated by the letter A; agents having little apparent effect are indicated by the letter B; the letter C indicates agents which appeared to dissipate the thread-like precipitates but resulted in cloudy solutions with small precipitates; and the letter D indicates agents that decreased the number and size of the thread-like precipitates. The addition of 0.1% TWEEN 20 to the $BPI_{23}$ solution provided the best effects. In a subsequent experiment 0.1% TWEEN 20 alone did not appear to dissipate the thread-like precipitate and 1% deoxycholate appeared to prompt precipitate formation.

TABLE 1

| AGENT | RESULT |
|---|---|
| 100 μL phospholipid (Culture PL, AH Labs) | A |
| 10 μL endotoxin suspension | A |
| 3 M thiocyanate | A |
| 2% taurine | A |
| 0.05% octoxynol-9 (TRITON X-100) | A |
| 2% lysine | A |
| 10% dimethylsulfoxide | A |
| 2% albumin | A |
| 20% glycerol | B |
| 2% glycine | B |
| 2 mM ethylenediamine tetra acetic acid | B |
| 5% polyethylene glycol | C |
| 30% acetic acid | C |
| 60% acetonitrile | C |
| 2% sodium dodecyl sulfate | C |
| 5% isopropanol | D |
| 10% ethanol | D |
| 0.1% polysorbate 80 (TWEEN 80) | D |
| 0.1% polysorbate 20 (TWEEN 20) | D |

An attempt was made to use liposome materials to dissipate thread-like precipitates in a solution of the recombinant expression product of a DNA sequence encoding the entire 456 amino acid residues of mature human BPI. The solution was sonicated with a lipid mixture (liposome kit, Sigma Chemical, St. Louis, Mo.) with little apparent effect on the precipitates.

1C. Elution into a Nonionic Detergent Solution

Washed beads according to Example 1A were eluted with Buffer into a tube which contained polysorbate 20 such that the final concentration of polysorbate 20 in the solution was 0.01%. The elution of sample directly into the polysorbate 20 solution appeared to drastically reduce the amount of hairy, thread-like precipitates in the preparation.

EXAMPLE 2

In this example, naturally-occurring BPI holoprotein and recombinant BPI fragments, analogs and variants thereof were subjected to assays to determine the effect of polysorbate 20 nonionic detergent on the biological activity of the protein. Compositions of such products with polysorbate 20 were variously tested in $E.\ coli$ growth inhibition assays, in an in vitro Limulus Amoebocyte lysate inhibition assay and in an in vivo LPS toxic challenge assay. The results showed that incorporation of polysorbate 20 nonionic detergent in the formulations had no detrimental effect on the biological activity in the assays.

2(A). $E.\ Coli$ Growth Inhibition Assays

In this example, $E.\ coli$ growth inhibition assays were conducted to determine the effect of polysorbate 20 on the biological activities of $rBPI_{23}$, naturally-occurring BPI holoprotein, $rBPI_{21}$ and rBPI-immunoglobulin fusion proteins according to Theofan et al. U.S. application Ser. Nos. 07/885,911 filed May 19, 1992 and 08/064,693 filed May 19, 1993. The results for combinations of polysorbate 20 with $rBPI_{23}$ set out below are representative of the results for the other BPI polypeptides and demonstrate the absence of any adverse effect by polysorbate 20 on $rBPI_{23}$ polypeptide. Broth assays were performed to compare the effect of formulations of $rBPI_{23}$ with 0.1% polysorbate 20 nonionic detergent (TWEEN 20) and formulations of $rBPI_{23}$ without polysorbate 20 on the growth of $E.\ coli$ J5, a rough UDP-galactose 4 epimerase negative mutant of the smooth $E.\ coli$ strain 0111-B4. In each assay, cells were grown overnight in TYE broth [Gazzano-Santoro et al., Infect. Immun., 60:4754 (1992)] and then subcultured in triethanolamine buffered minimum salt medium [TEA, Weiss et al. J. Clin. Invest., 65:619 (1980)]. The bacterial cells were harvested in late-logarithmic phase, centrifuged and resuspended in 0.9% NaCl to provide a suspension of about $5 \times 10^8$ cells/mL ($A_{600} \sim 0.5$). Aliquots of the suspension providing about $10^7$ cells were added to 0.4 mL of suspension medium [10 mL comprising 1.0 mL Hanks Balanced Salts Solution, 0.4 mL/M Tris-HCl (pH 7.5), 0.2 mL of 5% Casamino acids, 1.0 mL 9% NaCl and water to volume]. 20 μl buffered (20 mM Sodium Acetate, pH 4, 1.0 M NaCl) $rBPI_{23}$ test solutions at a concentration of 1 μg/mL and/or buffer controls were added to the cells, which were then incubated at 37° C. for 30 minutes. Dilutions of formulated $rBPI_{23}$ to 1 μg/ml were performed using buffer either with or without polysorbate 20 as indicated in Table 2 below. Four mL of nutrient broth [Difco Laboratories Inc., Detroit, Mich., 0.9% NaCl] was added to each sample. Tubes were incubated on a rotary shaker and read at $A_{600}$ at 2, 4 and 6 hours with the results shown in FIG. 1 wherein assay (1) is represented by the solid square; assay (2) is represented by the solid circle; assay (3) is represented by the solid triangle; assay (4) which overlaps with assay (5) is represented by an open square; and assay (5) which overlaps with assay (4) is represented by an open circle. The results of this experiment show that $rBPI_{23}$ in the presence of polysorbate 20 actually had greater cell growth inhibition activity than $rBPI_{23}$ in buffer without the nonionic detergent.

TABLE 2

Additives to Bacterial Cell Suspension

| Assay No. | BPI Preparation | BPI Diluent | Final BPI Conc. (μg/ml) |
|---|---|---|---|
| 1 | $rBPI_{23}$ in Acetate Buffer | Acetate Buffer | 1 |
| 2 | $rBPI_{23}$ in 0.1% TWEEN[1] | 0.1% TWEEN[1] | 1 |
| 3 | $rBPI_{23}$ in 0.1% TWEEN[1] | Acetate Buffer | 1 |
| 4 | Acetate Buffer | NA | 0 |
| 5 | 0.1% TWEEN[1] | NA | 0 |

[1]Acetate buffer containing 0.1% TWEEN 20.

Figure 2:
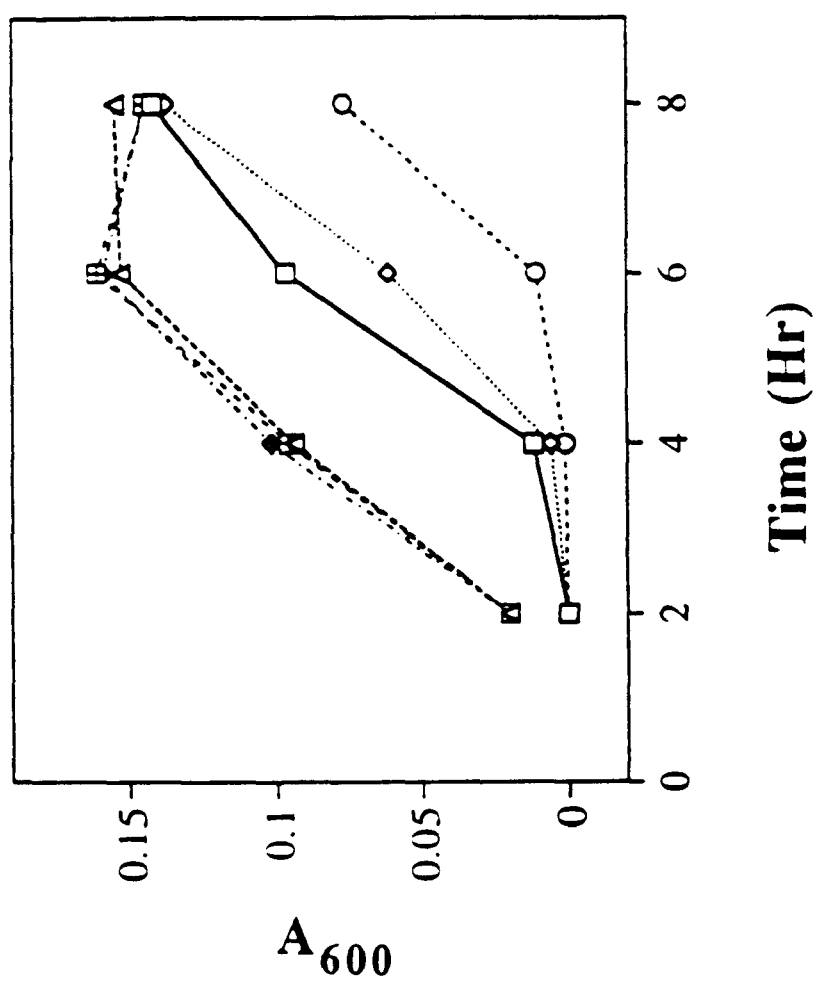

In a second series of experimental assays the $rBPI_{23}$ compositions set out in Table 3 below were tested in the same assay described above with the results shown in FIG. 2 wherein assay 1 is represented by an open square; assay 2 is represented by an open diamond; assay 3 is represented by an open circle; assay 4 is represented by an open triangle; assay 5 is represented by an open square containing a plus sign; and assay 6 is represented by an open diamond containing a plus sign. Results of assays 4, 5 and 6 are largely overlapping. The results of this experiment show that $rBPI_{23}$ in the presence of polysorbate 20 actually had greater cell growth inhibition activity than $rBPI_{23}$ in buffer without the nonionic detergent.

TABLE 3

Additive to Bacterial Cell Suspension

| Assay No. | BPI Preparation | BPI Diluent | Final BPI Conc. (μg/ml) |
|---|---|---|---|
| 1 | $rBPI_{23}$ in Acetate Buffer | Acetate Buffer | 1 |
| 2 | $rBPI_{23}$ in Acetate Buffer | Acetate Buffer[1] | 1 |

TABLE 3-continued

Additive to Bacterial Cell Suspension

| Assay No. | BPI Preparation | BPI Diluent | Final BPI Conc. (µg/ml) |
|---|---|---|---|
| 3 | rBPI$_{23}$ in 0.1% TWEEN[2] | 0.1% TWEEN | 1 |
| 4 | Acetate Buffer only | NA[3] | 0 |
| 5 | 0.1% TWEEN[2] only | NA[3] | 0 |
| 6 | Buffer only | NA[1,3] | 0 |

[1] 2 µl of 1% TWEEN added directly to cells in suspension medium.
[2] Acetate buffer containing 0.1% TWEEN 20.
[3] Not applicable.

2(B). In Vitro LAL Inhibition Assay

Figure 3:
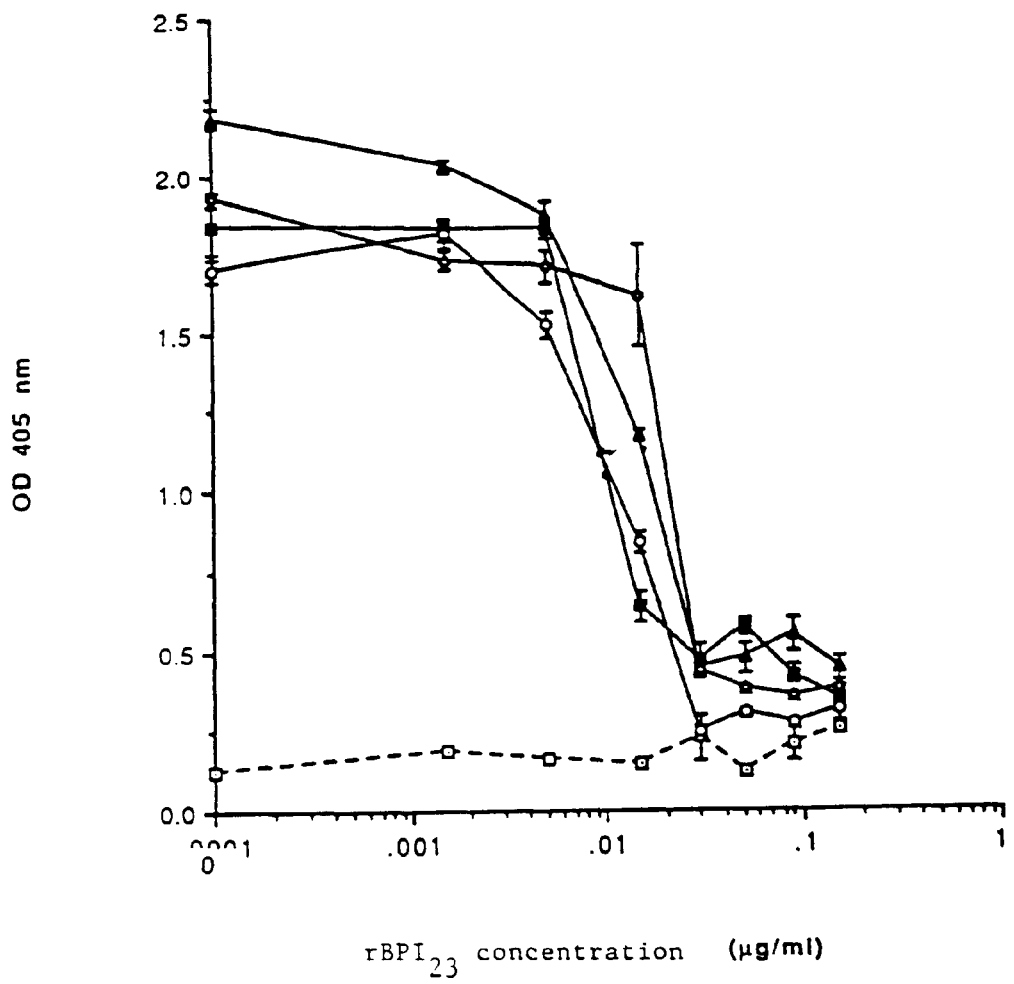
FIG. 3 depicts the results of a Limulus Amoebocyte Lysate (LAL) assay using $rBPI_{23}$ formulated in polysorbate 20.

Solutions comprising rBPI$_{23}$ were subjected to a Limulus Amoebocyte Lysate (LAL) inhibition assay to determine the effect of polysorbate 20 nonionic detergent on the LPS binding properties of rBPI$_{23}$. Specifically, an rBPI$_{23}$ preparation was obtained by elution with a 20 mM sodium acetate/acetic acid buffer at pH 4.0 and 0.7 M to 1.0 M NaCl from S-Sepharose beads cultured in roller bottles containing transfected CHO cells. The preparation was then (1) treated with polysorbate 20 (TWEEN 20) to a concentration of 0.05% (closed triangles in FIG. 3); (2) treated with sodium azide to a concentration of 0.02% (open circles in FIG. 3) or (3) left untreated (open diamonds in FIG. 3). A second rBPI$_{23}$ preparation comprising 0.4 mg/mL in 10 mM potassium phosphate pH 7.0, 0.15 M NaCl and 0.05% polysorbate 20 (closed squares in FIG. 3) was also used in the assay. The BPI preparations were mixed in Eppendorf tubes with a fixed concentration of E. coli 0113 LPS and incubated at 37° C. with occasional shaking. A control with no LPS (open squares in FIG. 3) was also tested. Following incubation, D-PBS was added to each tube to reduce the LPS concentration for the LAL assay. Each sample was then transferred into Immulon II strips (Dynatech, Chantilly, Va.) in volumes of 50 µl per well.

Limulus amoebocyte Lysate (Quantitative chromogenic LAL kit, Whitaker Bioproducts, Inc., Walkersville, Md.) was added to each well according to the kit instructions and the wells were incubated at room temperature. Chromogenic substrate was then added to each well and was mixed well with the contents. After incubation at room temperature, the reaction was stopped with addition of 25% acetic acid. Optical density at 405 nm was then measured in a multiplate reader (Vmax, Molecular Dynamics, Menlo Park, Calif.) with the results shown in FIG. 3. Inhibition of LPS activation of LAL by rBPI$_{23}$ is indicated by the concentration-dependent drop in OD$_{405}$.

The results show that the inclusion of polysorbate 20 had no detrimental effect on the biological activity of rBPI$_{23}$ in the assay.

2(C). In Vivo LPS Toxic Challenge Assay

In this example, a study was conducted to assess the efficacy of rBPI$_{23}$ formulated with polysorbate 20 nonionic detergent lipid carrier in an actinomycin-D sensitized mouse model according to Pieroni et al., Proc. Soc. Exp. Biol. & Med.; 133, 790 (1970). ICR mice were administered an intravenous injection of actinomycin-D (800 µg/kg). Immediately thereafter, a group of 15 mice received injections of 100 µg/kg E. coli 0111:B4 LPS and 3.8 mg/kg rBPI$_{23}$ in a composition comprising 10 mM potassium phosphate 0.17 M NaCl pH 4.0 and 0.05% polysorbate 20. As controls, some animals were treated with buffer but not BPI and other animals were treated with actinomycin D but not with the LPS or BPI.

The results presented in Table 4 show that no deaths occurred in the control animals not treated with LPS and that fewer deaths occurred in the animals treated with rBPI$_{23}$ formulated with polysorbate 20 (13/15) than in the animals treated with buffer (15/15).

TABLE 4

| E. coli 0.111:B4 µg/kg | Act-D 800 µg/kg | rBPI$_{23}$ 3.8 mg/kg | No. Dead/ Total |
|---|---|---|---|
| 0 | + | − | 0/15 |
| 100 | + | − | 15/15 |
| 100 | + | + | 13/15 |

EXAMPLE 3

In this example, tests of various surfactants were conducted to determine their utility for surface stabilization of a recombinant BPI fragment polypeptide pharmaceutical (rBPI$_{23}$). The rBPI$_{23}$ was provided at a concentration of 1 mg/mL in citrate buffered saline (0.02 M citrate, 0.15 M NaCl, pH 5.0). Various surfactants were then added to this preparation in order to determine their utility as stabilizers.

According to this test, rBPI$_{23}$ was filled by hand to 5 mL in sealed sterile 5 mL molded glass vials (total capacity 8.4 mL, Wheaton) in the desired formulation buffer. The vials to be tested were set horizontally on a flat bed shaker (S/P rotor V) and fixed to the shaker by tape. Vials were then shaken at 150 rpm at room temperature. At 0 hours, 2–4 hours, and 18 hours, 150 µl samples were withdrawn in a biosafety cabinet using a 1 mL syringe fitted with a 21 gauge needle. The starting, in process, and ending soluble rBPI$_{23}$ concentrations were determined by an ion exchange HPLC assay and visual observation of cloudiness of the solution was also recorded. The results are shown below in Table 6 in which acceptable stability was determined by visual inspection after the shake test.

Testing of protein preparations comprising single surfactants showed good results for use of octoxynol-9 (TRITON X-100, Rohm & Haas), laureth-4, (BRIJ 30, ICI Americas), poloxamer 403 (PLURONIC P123, BASF Wyandotte) and telomere B monoether with polyethylene glycol (ZONYL FSO-100, E. I. DuPont de Nemours).

Testing of other surfactants as shown in Table 5 shows that surfactants producing a surface tension lower than 35 mN/m are capable of stabilizing rBPI at surfactant concentrations of 0.1%. This example further shows that both polysorbate 80 (TWEEN 80) and poloxamer 188 (PLURONIC F-68) were incapable of stabilizing the protein preparation alone under the shake test conditions employed. The incorporation of polysorbate 80 did, however, have the effect of clarifying a cloudy solution of BRIJ 30 which is not readily water soluble without the help of an additional solubilizer.

TABLE 5

| Exp No. | Surfactant Used | Surface Tension mN/m at 0.1% Conc. at Room Temp. in Water (w), Buffer (b)[1] | Surfactant Concentration in Form. Buffer | Visual Observation 3–4 hr | Visual Observation 18 hr | rBPI$_{23}$ Conc. by HPLC (mg/mL) 0 hr | rBPI$_{23}$ Conc. by HPLC (mg/mL) 3–4 hr | rBPI$_{23}$ Conc. by HPLC (mg/mL) 18 hr |
|---|---|---|---|---|---|---|---|---|
| 1 | ZONYL FSO-100 | 17[w] | 0.100% | — | Clear | 0.96 | — | 1.00 |
| 2 | PS-80 | 41[b] | 0.100% | — | Cloudy | 1.11 | — | 0.02 |
| 3 | BRIJ 30 | 27.5[b] | 0.500% | Cloudy | Cloudy[2] | 1.08 | — | 1.14 |
| 4 | TRITON X-100 | 32[b] | 0.100% | Clear | Clear | 1.00 | 1.01 | 0.98 |
| 5 | PLUR P123 | 34.3[w] | 0.100% | Clear | Clear | 1.08 | 1.08 | 1.08 |
| 6 | BRIJ 30/PS-80 | — | 0.1%/0.125% | Clear | Clear | 1.19 | 1.21 | 1.17 |
| 7 | PLUR F-68 | 46[b] | 0.100% | Clear | Haze; specks. | 1.23 | 1.22 | 0.95 |
| 8 | PLUR F-68 | 44[b] | 0.200% | Clear | Haze with a few specks. | — | — | 1.04 |

[1]Surface tensions with superscript w are obtained from the surfactant manufacturer. Surface tensions with superscript b are obtained experimentally using Wilhelny plate method.
[2]Brij 30 alone is cloudy.

EXAMPLE 4 in this example, additional comparisons were carried out according to the methods of Example 3 using various surfactants alone to stabilize a rBPI$_{23}$ preparation. The results are shown below in Table 6 in which acceptable stability was determined by visual inspection after the shake test.

TABLE 6

| Exp No. | Surfactant Used | Surfactant Conc. in Form. Buffer | Visual Observation 3–4 hr | Visual Observation 18 hr | Conc. by HPLC (mg/mL) 0 hr | Conc. by HPLC (mg/mL) 3–4 hr | Conc. by HPLC (mg/mL) 18 hr |
|---|---|---|---|---|---|---|---|
| 1 | ZONYL FSO-100 | 0.100% | — | Clear | 0.96 | — | 1.00 |
| 2 | PS-80 | 0.100% | — | Cloudy | 1.11 | — | 0.02 |
| 3 | Dextran Sulfate | 1 mg/mL | — | Cloudy | — | — | 0.00 |
| 4 | Glycerol | 10.0% | — | Cloudy | 0.86 | — | 0.02 |
| 5 | HSA | 5.0% | — | Cloudy | 0.92 | — | 0.00 |
| 6 | Control—5 mL Fill Volume | — | — | Cloudy | 1.13 | — | 0.03 |
| 7 | Control 8.4 mL (complete) Fill Volume | — | — | Clear. One speck of precipitate. | 1.13 | — | 1.04 |
| 8 | Control—5 mL (partial) Fill Volume | — | Cloudy | Cloudy | 1.16 | 0.21 | 0.00 |
| 9 | TRITON X-100 | 0.500% | Clear | Clear | 1.04 | 0.99 | 1.11 |
| 10 | PS-80 | 0.500% | Clear | Cloudy | 1.12 | 0.95 | 0.59 |
| 11 | PLURONIC P123 | 0.500% | Clear | Clear | 1.15 | — | 1.13 |
| 12 | BRIJ 30 | 0.500% | Cloudy[1] | Cloudy[1] | 1.08 | — | 1.14 |
| 13 | TRITON X-100 | 0.100% | Clear | Clear | 1.00 | 1.01 | 0.98 |
| 14 | TRITON X-100 | 0.010% | Slt. Haze | Cloudy | 0.96 | 0.84 | 0.04 |
| 15 | PLURONIC P123 | 0.100% | Clear | Clear | 1.08 | 1.08 | 1.08 |
| 16 | PLURONIC P123 | 0.100% | Clear | Clear | 1.23 | 1.26 | 0.94 |
| 17 | PLURONIC P123 | 0.050% | Clear | Slt. Haze | 1.21 | 1.18 | 1.11 |
| 18 | PLURONIC P123 | 0.010% | Cloudy | Cloudy | 1.14 | 0.00 | 0.00 |
| 19 | BRIJ 30/PS-80 | 0.1%/0.125% | Clear | Clear | 1.19 | 1.21 | 1.17 |

TABLE 6-continued

| Exp No. | Surfactant Used | Surfactant Conc. in Form. Buffer | Visual Observation | | Conc. by HPLC (mg/mL) | | |
|---|---|---|---|---|---|---|---|
| | | | 3–4 hr | 18 hr | 0 hr | 3–4 hr | 18 hr |
| 20 | BRIJ 30/ PS-80 | 0.075%/ 0.094% | Clear | Clear | 1.22 | 1.20 | 1.18 |
| 21 | BRIJ 30/ PS-80 | 0.03%/ 0.038% | Slt. Haze | Cloudy | 1.20 | 1.05 | 0.41 |
| 22 | BRIJ 30/ PS-80 | 0.01%/ 0.013% | Cloudy | Cloudy | 1.14 | 0.48 | 0.00 |
| 23 | PLURONIC F68 | 0.100% | Clear | Slt. Haze | 1.23 | 1.22 | 0.95 |
| 24 | PLURONIC F68 | 0.100% | Clear | Slt. Haze | — | — | 1.00 |
| 25 | PLURONIC F68 | 0.150% | Clear | Slt. Haze | — | — | 1.06 |
| 26 | PLURONIC F68 | 0.200% | Clear | Slt. Haze | — | — | 1.04 |
| 27 | PLURONIC F68 | 0.300% | Clear | Slt. Haze | — | — | 1.10 |
| 28 | PLURONIC F68 | 0.500% | Clear | Slt. Haze | — | — | 1.08 |
| 29 | PLURONIC P123 | 0.070% | Clear | Clear | 1.06 | 1.08 | 0.97 |
| 30 | BRIJ 30/ PS-80 | 0.05%/ 0.063% | Clear | Clear | 1.04 | 1.01 | 1.01 |
| 31 | PLURONIC F88 | 0.100% | Cloudy | Cloudy | 1.07 | 0.87 | 0.56 |
| 32 | PLURONIC F98 | 0.100% | Cloudy | Cloudy | 1.04 | 0.77 | 0.39 |
| 33 | PLURONIC F108 | 0.100% | Clear | Cloudy | 1.04 | 0.87 | 0.55 |
| 34 | PLURONIC F127 | 0.100% | Clear | Clear | 1.06 | 1.04 | 0.98 |
| 35 | PLURONIC F127 | 0.100% | Clear | Clear | 1.12 | — | 0.93 |
| 36 | PLURONIC F127 | 0.075% | Clear | Clear | 1.10 | — | 0.61 |
| 37 | PLURONIC F127 | 0.050% | Clear | Slt. Haze | 1.09 | — | 0.20 |
| 38 | PLURONIC F127 | 0.025% | Slt. Haze | Cloudy | 1.07 | — | 0.00 |
| 39 | PLURONIC F127 | 0.010% | Cloudy | Cloudy | 1.06 | — | 0.00 |

[1]Brij 30 alone is cloudy.

EXAMPLE 5

In this example surface tension measurements were made of polysorbate and poloxamer surfactants alone, or combinations of the two in solutions of the BPI protein product rBPI$_{21}$ according to the procedure set out in the Krüss Digital Tensiometer K10ST Users Manual, Chapter 4: Measuring with the Plate. A decrease in surface tension indicates an increase in the surface activity of the surfactant, which has conventionally been thought to be the mechanism by which surfactants stabilize proteins. These procedures established that poloxamer surfactants provide advantageous results by a different and unexpected mechanism.

Specifically, a 2 mg/mL solution of unformulated rBPI$_{21}$ (lot 30216) was diluted with 20 mM sodium citrate, 150 mM sodium chloride, pH 5.0 rendering a 1 mg/mL solution. 15 mL of this solution was placed into a 50 mL glass beaker containing a mini stir bar. Surfactants poloxamer 188, polysorbate 80, or combinations of both were added incrementally up to 0.10%. Before each surface tension measurement, the platinum plate was heated above the reducing zone (blue flame) of a gas burner until the plate just began to glow red. The platinum plate was heated for about 10 to 15 seconds while turning the plate from side to side and then suspended back into the instrument. Each addition of surfactant was gently mixed using a magnetic stirrer and the solution was allowed to stand for 2 minutes on the thermostat vessel equilibrated at 4.6° C. The value for the surface tension was read after five minutes.

Figure 4:
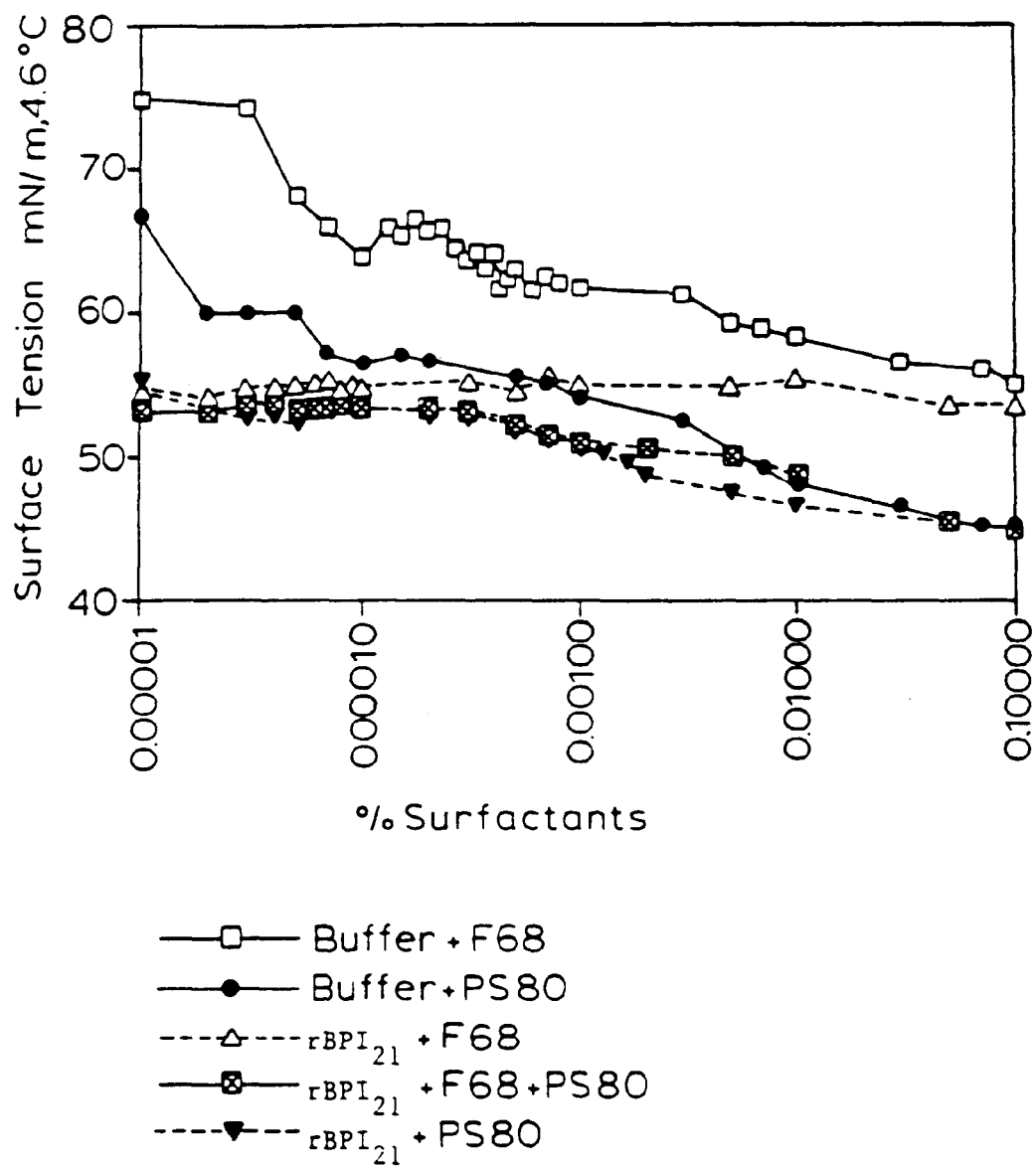
FIG. 4 is a graph depicting surface tension measurements of $rBPI_{21}$ solutions with varying surfactant concentrations of polysorbate 80 (PS80) and poloxamer 188 (F68).

The first part of this experiment evaluated the surface activity of the surfactants alone in buffer. Using the citrate saline buffer (20 mM sodium citrate, 150 mM sodium chloride, pH 5.0) as the baseline, surfactants were added incrementally. FIG. 4 is a plot of surface tension dependence on surfactant concentrations; the corresponding data is presented in Table 7. The open squares represent the citrate saline buffer in varying concentrations of poloxamer 188 while the closed circles represent the same buffer in varying concentrations of polysorbate 80. The citrate-saline buffer solution alone had a surface tension of about 75 mN/m at 4.6° C., similar to $H_2O$. With increasing concentrations of surfactants, the buffer solution showed decreasing surface tension. With 0.10% poloxamer 188, the surface tension of the solution was 55 mN/m. On the other hand, with 0.10% polysorbate 80, the surface tension of the solution was 45 mN/m. The decrease in surface tension indicates an increase in the surface activity of the surfactant, i.e., the lower the surface tension, the higher the surface activity. The results indicate that polysorbate 80 is more surface active than poloxamer 188.

In the second part of the experiment, the surface activity of rBPI$_{21}$ in the presence of surfactants was evaluated. The results show that $rBPI_{21}$ at 1 mg/mL in citrate saline buffer, pH 5.0; is surface active with a surface tension of about 54 mN/m at 4.6° C. The addition of polysorbate 80 (PS80) alone up to 0.0005% did not change the surface tension of $rBPI_{21}$ solution either (FIG. 4, closed triangles). At concentrations of polysorbate 80 exceeding 0.0005%, the surface tension of $rBPI_{21}$ follows that of buffer with PS80 alone (no BPI), in which the surface tension of the solution decreases as the concentration of polysorbate 80 is gradually increased. For buffer with PS80 alone, the surface tension of 54 mN/m was reached when the PS80 concentration was increased from 0.0005%. These results indicate that when PS80 concentration is less than 0.0005%, the surface activity of the solution is dominated by $rBPI_{21}$. On the other hand, at PS80 concentrations above 0.0005%, the surface activity of the solution is modulated by polysorbate 80. The addition of poloxamer 188 (F68) alone to $rBPI_{21}$ at concentrations up to 0.10% did not change the surface activity of $rBPI_{21}$ solution significantly (FIG. 4, open triangles). Addition of varying concentrations of polysorbate 80 to an $rBPI_{21}$ solution containing 0.1% poloxamer 188 is represented by the closed squares in FIG. 4.

solutions was also prepared with surfactants at the same concentrations as in the $rBPI_{21}$ solutions to serve as blanks for DSC. Each solution was filtered and placed into a 2 mL sterile plastic vial. The samples were packed into a 4° C. cold box until subjected to DSC analysis.

The behavior of $rBPI_{21}$ was evaluated as the temperature of the solution was gradually increased from ambient temperature to about 90° C., at a rate of 1° C. per minute. As the temperature is increased two events occur. The first event is an unfolding reaction, which is endothermic, and is illustrated by an upward peak in the scans. The second event is precipitation, which is exothermic, and is depicted by a downward peak in the scans. In the scans depicted in FIGS. 5, 6 and 8–10, each scan is offset to facilitate analysis of data. In the $rBPI_{21}$ solution not containing surfactants (FIG. 5, Scan 1) the unfolding of the protein at 65° C. was followed immediately by the second event, precipitation of the protein at 66 to 67° C.

With low poloxamer 188 (PLURONIC® F68) concentrations ranging between 0.001% to 0.01%, the unfolding and precipitation events are similar to the $rBPI_{21}$ solution without surfactants (FIG. 5, Scans 2 to 5), i.e. as $rBPI_{21}$ unfolds,

TABLE 7

| | 1 % F68 | 2 Buffer + F68 (mN/m) | 3 % PS80 | 4 Buffer + PS80 (mN/m) | 5 % F68 | 6 $rBPI_{31}$ + F68 (mN/m) | 7 % PS80 | 8 $rBPI_{31}$ + 0.1% F68 + PS80 (mN/m) | 9 % PS80 | 10 $rBPI_{31}$ + PS80 (mN/m) |
|---|---|---|---|---|---|---|---|---|---|---|
| 1 | 0.00000 | 75.4 | 0.00000 | 75.1 | 0.00000 | 54.2 | 0.00000 | 53.7 | 0.00000 | 54.9 |
| 2 | 0.00001 | 74.9 | 0.00001 | 66.8 | 0.00001 | 54.7 | 0.00001 | 53.4 | 0.00001 | 55.0 |
| 3 | 0.00003 | 74.3 | 0.00002 | 60.0 | 0.00002 | 54.2 | 0.00002 | 53.3 | 0.00002 | 53.2 |
| 4 | 0.00005 | 68.2 | 0.00003 | 60.0 | 0.00003 | 54.9 | 0.00003 | 53.9 | 0.00003 | 53.3 |
| 5 | 0.00007 | 65.9 | 0.00005 | 60.0 | 0.00004 | 54.8 | 0.00004 | 53.9 | 0.00004 | 52.8 |
| 6 | 0.00010 | 64.0 | 0.00007 | 57.4 | 0.00005 | 55.0 | 0.00005 | 53.5 | 0.00005 | 52.4 |
| 7 | 0.00013 | 65.8 | 0.00010 | 56.6 | 0.00006 | 55.2 | 0.00006 | 53.5 | 0.00006 | 53.3 |
| 8 | 0.00015 | 65.4 | 0.00015 | 57.2 | 0.00007 | 55.4 | 0.00007 | 53.4 | 0.00007 | 53.6 |
| 9 | 0.00017 | 66.5 | 0.00020 | 56.7 | 0.00008 | 54.8 | 0.00008 | 53.8 | 0.00008 | 53.8 |
| 10 | 0.00020 | 65.7 | 0.00050 | 55.6 | 0.00009 | 55.0 | 0.00010 | 53.4 | 0.00009 | 53.2 |
| 11 | 0.00023 | 66.0 | 0.00070 | 55.3 | 0.00010 | 54.9 | 0.00020 | 53.5 | 0.00010 | 53.5 |
| 12 | 0.00027 | 64.4 | 0.00100 | 54.2 | 0.00030 | 55.3 | 0.00030 | 53.2 | 0.00020 | 53.2 |
| 13 | 0.00030 | 63.8 | 0.00300 | 52.7 | 0.00050 | 54.5 | 0.00050 | 52.3 | 0.00030 | 53.0 |
| 14 | 0.00033 | 64.1 | 0.00700 | 49.2 | 0.00070 | 55.5 | 0.00070 | 51.5 | 0.00050 | 52.0 |
| 15 | 0.00037 | 63.1 | 0.01000 | 48.3 | 0.00100 | 54.9 | 0.00100 | 51.0 | 0.00070 | 51.2 |
| 16 | 0.00040 | 64.2 | 0.03000 | 46.5 | 0.00500 | 54.9 | 0.00200 | 50.6 | 0.00100 | 50.5 |
| 17 | 0.00043 | 61.8 | 0.07000 | 45.3 | 0.01000 | 55.4 | 0.00500 | 50.1 | 0.00130 | 50.4 |
| 18 | 0.00047 | 62.4 | 0.10000 | 45.4 | 0.05000 | 53.6 | 0.01000 | 48.6 | 0.00170 | 49.8 |
| 19 | 0.00050 | 63.1 | | | 0.10000 | 53.7 | 0.05000 | 45.6 | 0.00200 | 48.8 |
| 20 | 0.00060 | 61.6 | | | | | 0.10000 | 45.0 | 0.00500 | 47.7 |
| 21 | 0.00070 | 62.5 | | | | | | | 0.01000 | 46.7 |
| 22 | 0.00080 | 62.0 | | | | | | | 0.05000 | 45.4 |
| 23 | 0.00100 | 61.7 | | | | | | | 0.10000 | 45.0 |
| 24 | 0.00300 | 61.2 | | | | | | | | |
| 25 | 0.00500 | 59.3 | | | | | | | | |
| 26 | 0.00700 | 58.9 | | | | | | | | |
| 27 | 0.01000 | 58.4 | | | | | | | | |
| 28 | 0.03000 | 56.6 | | | | | | | | |
| 29 | 0.07000 | 56.1 | | | | | | | | |
| 30 | 0.10000 | 55.1 | | | | | | | | |

EXAMPLE 6

Figure 5:
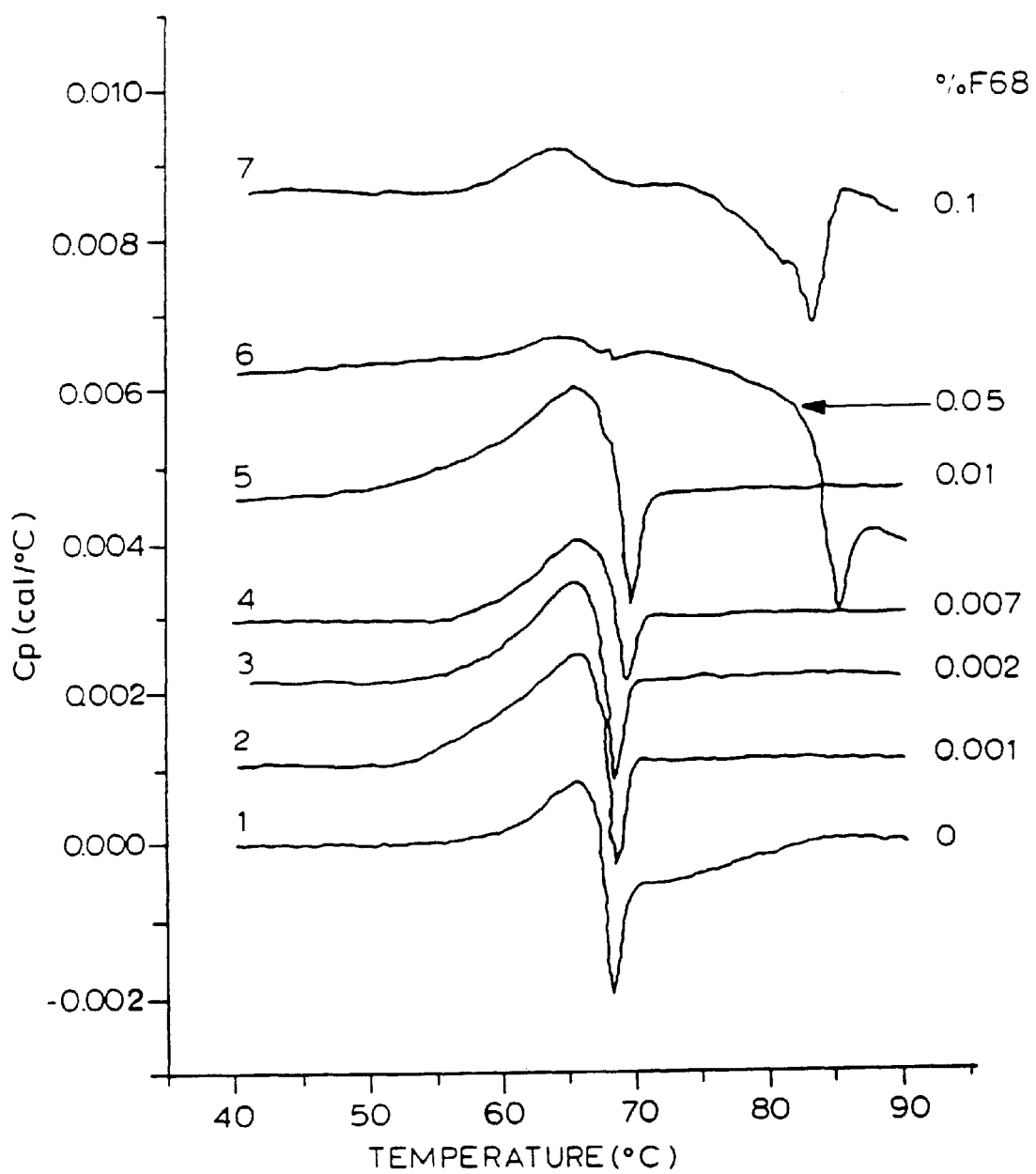
FIG. 5 is a series of graphs of differential scanning calorimetry results of $rBPI_{21}$ with various concentrations of the surfactant poloxamer 188 (F68).
Figure 6:
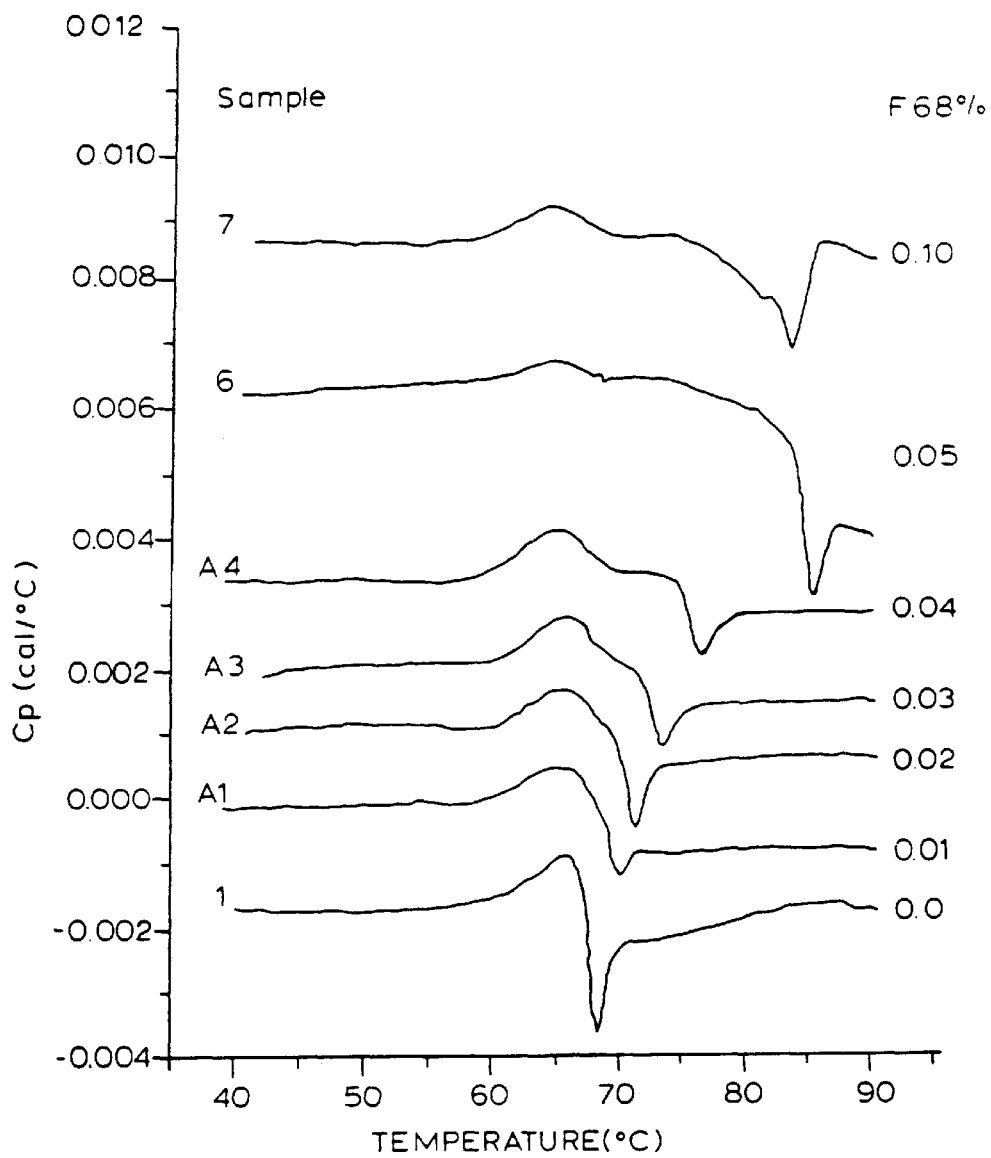
FIG. 6 is another series of graphs of differential scanning calorimetry results of $rBPI_{21}$ with various concentrations of poloxamer 188 (F68).
Figure 7:
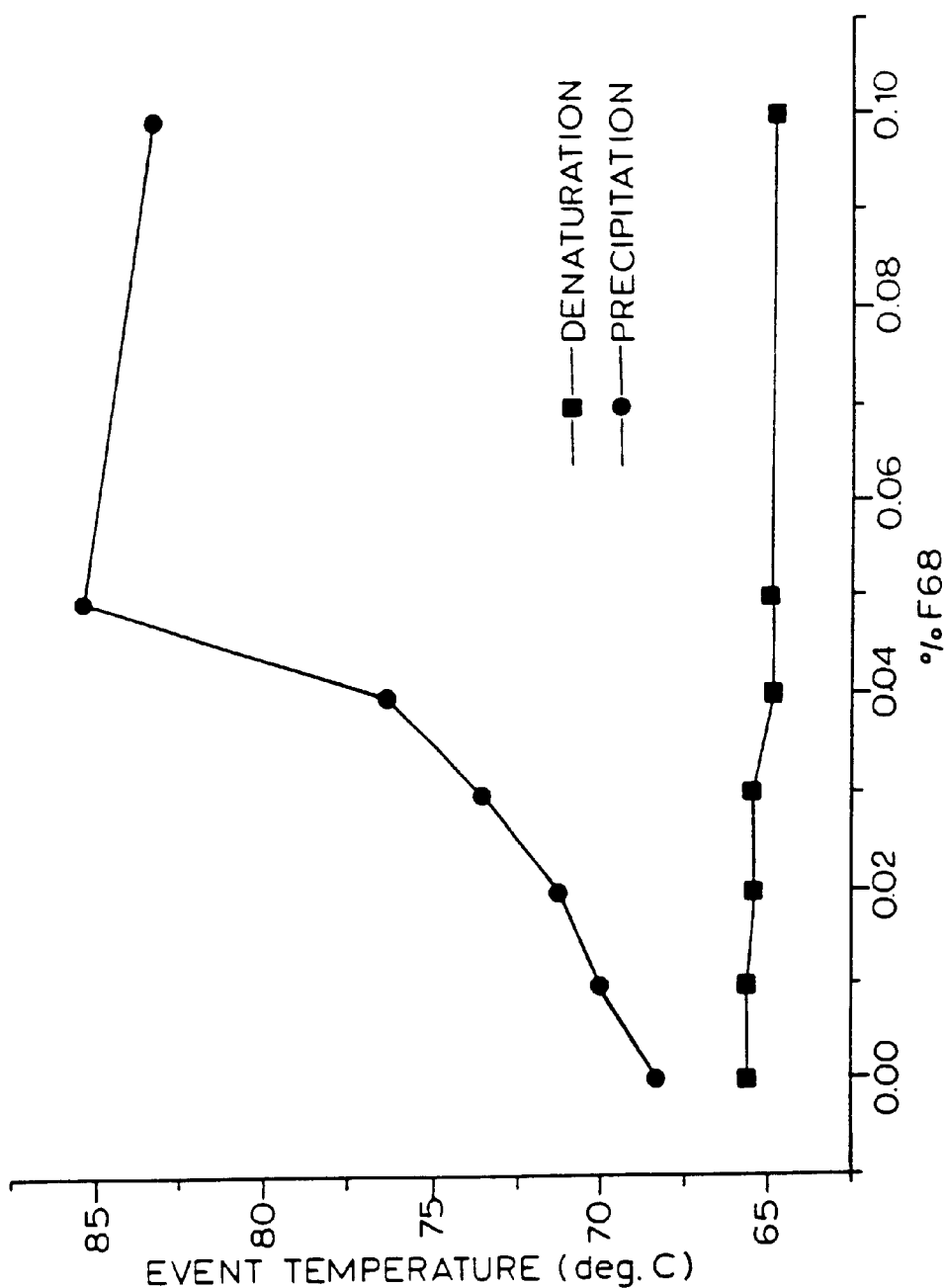
FIG. 7 is a plot showing the change in denaturation and precipitation temperatures of $rBPI_{21}$ over varying concentrations of the surfactant poloxamer 188 (F68).
Figure 8:
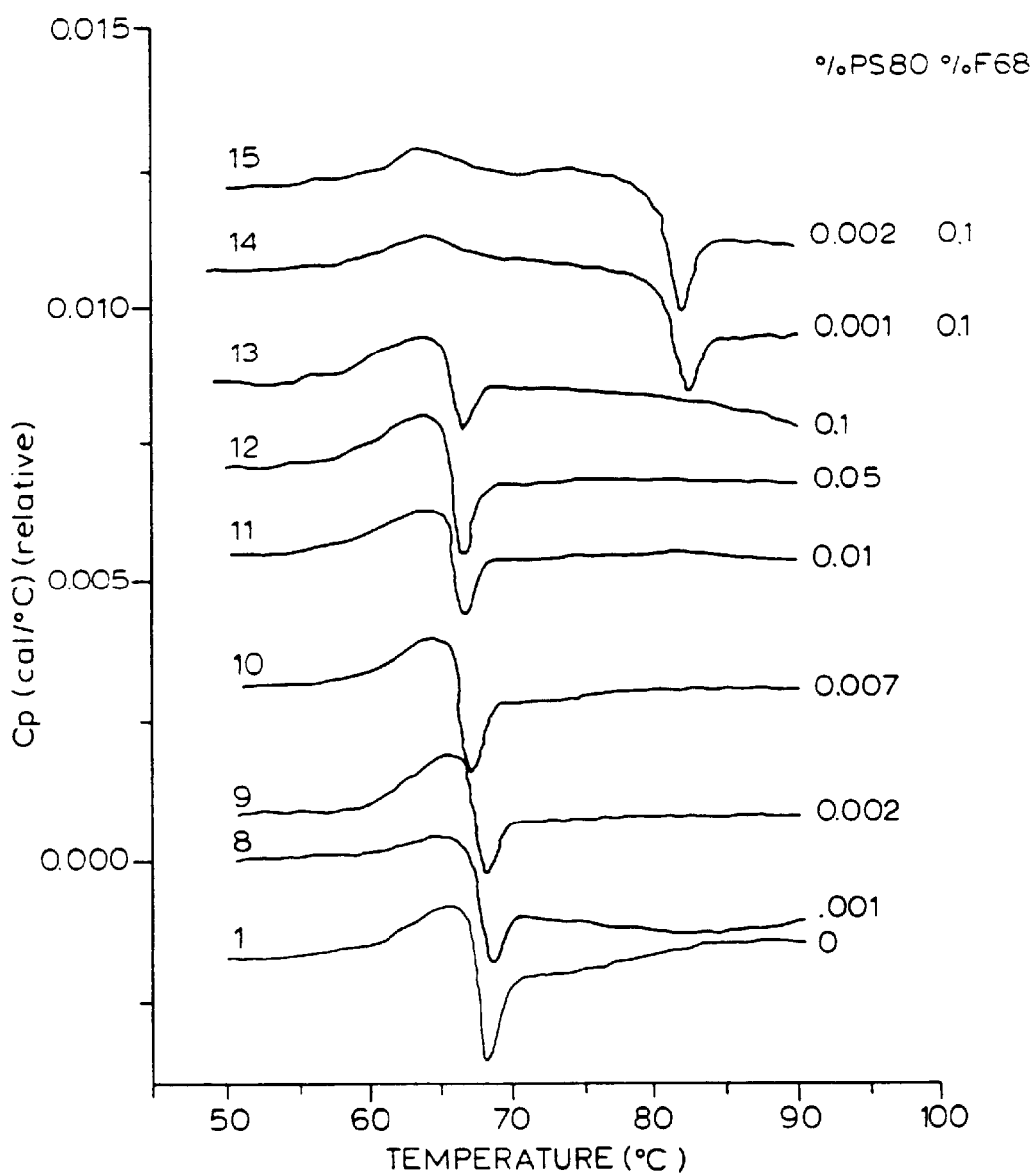
FIG. 8 is a series of graphs of differential scanning calorimetry results of $rBPI_{21}$ with various concentrations of polysorbate 80 (PS80) alone or in combination with 0.1% poloxamer 188 (F68) by weight.
Figure 9:
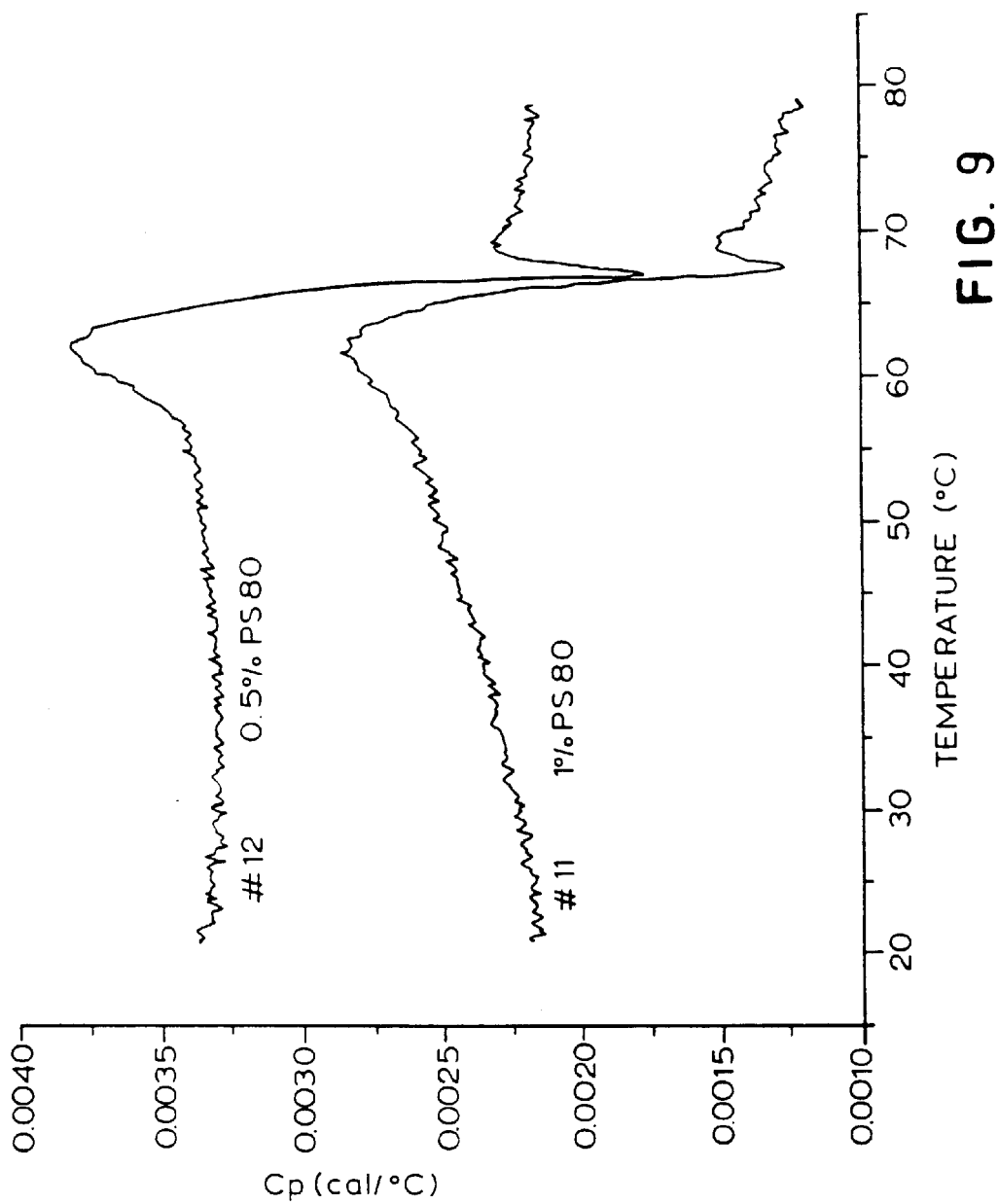
FIG. 9 is a set of graphs of differential scanning calorimetry results of $rBPI_{21}$ with the surfactant polysorbate 80 (PS80) at two different concentrations.

Protein samples were analyzed by Differential Scanning Calorimetry (DSC) to study the unfolding (or denaturation) of the protein. The starting materials for DSC analysis were identical to those used in the surface tension measurement. A series of $rBPI_{21}$ solutions was prepared with varying concentrations of surfactants, poloxamer 188, polysorbate 80 or combinations of both, and diluted with buffer (20 mM sodium citrate, 150 mM sodium chloride, pH 5.0) to give a final $rBPI_{21}$ concentration of 1 mg/mL. A series of buffer precipitation takes place immediately. With poloxamer 188 concentrations exceeding 0.05%, the unfolding of $rBPI_{21}$ still occurs at 65° C., but precipitation does not occur until the temperature reaches 85° C. (FIG. 5, Scan 6). FIG. 6 shows that at poloxamer 188 concentrations between 0.01% and 0.05%, there is a gradual transition of delayed precipitation of unfolded BPI. These results suggest that at poloxamer 188 concentrations higher than 0.01%, unfolded $rBPI_{21}$ can be stabilized and the occurrence of precipitation is delayed. A plot of denaturation and precipitation temperature dependence over varying poloxamer 188 concentration is shown in FIG. 7. The effects of poloxamer 188 appear to delay the precipitation of rBPI$_{21}$ to a higher temperature but not to stabilize its native structure as the T$_m$ (denaturation temperature) and ΔH (energy of denaturation) did not change.

rBPI$_{21}$ formulated with polysorbate 80 at concentrations up to 1% was likewise analyzed by DSC (FIG. 8: Scans 1 and 8–13, FIG. 9: Scans 11, 12). The isotherms were similar to rBPI$_{21}$ solution without surfactants. Polysorbate 80 did not maintain the rBPI$_{21}$ in solution at higher temperatures. The stabilization of unfolded rBPI$_{21}$ is thus unique to poloxamer 188.

The two formulations using combined poloxamer 188 and polysorbate 80, namely 0.1%F68/0.001%PS80 and 0.1%F68/0.002%PS80 (FIG. 8, Scans 14, 15), showed the same scan profile as rBPI$_{21}$ containing 0.05% and 0.1% PLURONIC F68, with unfolding at 65° C. and precipitation at 85° C. (FIG. 6, Scans 6, 7).

Figure 10:
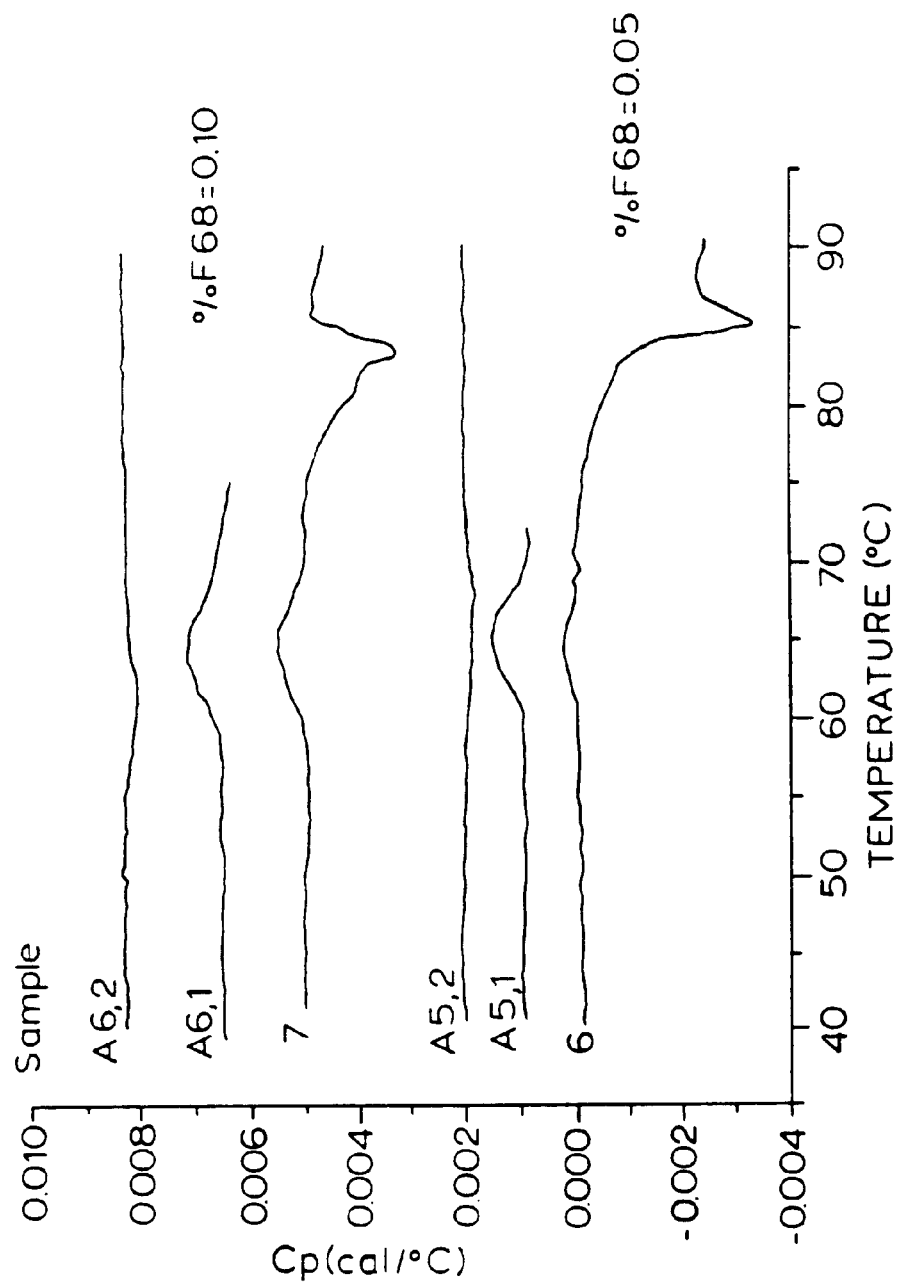
FIG. 10 is a set of graphs of differential scanning calorimetry results after a solution of $rBPI_{21}$ and poloxamer 188 (F68) was heated to a temperature higher than the denaturation/unfolding temperature but lower than the precipitation temperature, and then was cooled for repeat scanning.

In addition to determining the melting behavior of rBPI$_{21}$, rescanning was done with rBPI$_{21}$ formulations containing 0.05% and 0.10% poloxamer 188 to determine if unfolding is a reversible process. The temperature of the rBPI$_{21}$ solution was first increased to 75° C. (temperature after denaturation/unfolding but before precipitation), then was cooled down for repeat scanning. FIG. 10 shows that the addition of poloxamer 188 to rBPI$_{21}$ does not make unfolding reversible. Profiles A5,1 and A6,1 show the scanning to 75° C., while profile A5,2 and A6,2 are repeat scanning after cooling the system from 75° C. If unfolding were a reversible process, scan profiles 6 and 7 would have been obtained.

The experimental results described above demonstrate that poloxamer surfactant alone is capable of stabilizing BPI-related polypeptides in solution and delaying the occurrence of precipitation by a mechanism that does not appear to involve modulation of the surface tension of the aqueous solution. This property is unique to poloxamer because other surfactants which are detergents such as polysorbate 80 affect the precipitation phenomenon by modulation of the surface tension of the aqueous solution.

Numerous modifications and variations of the above-described invention are expected to occur to those of skill in the art. Accordingly, only such limitations as appear in the appended claims should be placed thereon.

What is claimed is:

1. A composition comprising a bactericidal/permeability-increasing protein (BPI) or a biologically active BPI fragment, BPI analog or BPI variant thereof and a lipid carrier wherein the BPI or biologically active BPI fragment, BPI analog or BPI variant thereof is solubilized in the lipid carrier.

2. The composition of claim 1 wherein the lipid carrier is polysorbate 80.

* * * * *